United States Patent [19]
Beitz

[11] Patent Number: 5,436,004
[45] Date of Patent: Jul. 25, 1995

[54] ADMINISTRATION OF CHOLESTEROL REDUCTASE TO HUMANS

[75] Inventor: Donald C. Beitz, Ames, Iowa

[73] Assignee: Iowa State University Research Foundation, Inc., Ames, Iowa

[21] Appl. No.: 796,403

[22] Filed: Nov. 22, 1991

Related U.S. Application Data

[63] Continuation-in-part of Ser. No. 339,229, Apr. 17, 1989, abandoned, which is a continuation-in-part of Ser. No. 222,016, Jul. 21, 1988, Pat. No. 4,921,710.

[51] Int. Cl.⁶ .............................................. A61K 38/54
[52] U.S. Cl. ..................... 424/94.4; 424/94.1; 424/493; 424/496; 424/497; 435/189; 426/56
[58] Field of Search .................. 424/94.3, 94.4, 195.1, 424/490, 491, 488, 463, 486, 493, 496, 497; 435/189; 426/56

[56] References Cited

U.S. PATENT DOCUMENTS

| | | | |
|---|---|---|---|
| 2,697,106 | 12/1954 | Shepherd et al. | 260/397.2 |
| 2,813,879 | 11/1957 | Wildi et al. | 260/397.2 |
| 2,838,526 | 6/1958 | Laubach | 260/397.2 |
| 2,979,440 | 4/1961 | Smythe | 195/64 |
| 3,959,540 | 5/1976 | Leiberich et al. | 428/35 |
| 4,001,480 | 1/1977 | Shank | 428/411 |
| 4,009,076 | 2/1997 | Green et al. | 195/63 |
| 4,079,125 | 3/1978 | Sipos | 424/32 |
| 4,106,991 | 8/1978 | Markussen et al. | 195/63 |
| 4,251,387 | 2/1981 | Lim et al. | 252/316 |
| 4,348,384 | 9/1982 | Horikoshi et al. | 424/101 |
| 4,362,711 | 12/1982 | Cerani | 424/33 |
| 4,482,630 | 11/1984 | Allen et al. | 435/187 |

OTHER PUBLICATIONS

Lehninger "Biochemistry," Second Edition, Worth Publichsers, Inc., (1975), p. 685.
Guyton, "Textbook of Medical Physiology" Fifth Edition, W. B. Saunders Company, (1976), pp. 924 & 925.

*Primary Examiner*—Michael G. Wityshyn
*Assistant Examiner*—C. Sayala
*Attorney, Agent, or Firm*—Zarley, McKee, Thomte, Voorhees, & Sease

[57] ABSTRACT

Cholesterol reductase is administered to humans to convert cholesterol to coprostanol in the small intestine thus decreasing the bloodstream cholesterol level.

6 Claims, 1 Drawing Sheet

ADMINISTRATION OF CHOLESTEROL REDUCTASE TO HUMANS

CROSS-REFERENCE TO RELATED APPLICATION

This application is a continuation-in-part of commonly assigned application Ser. No. 339,229, filed Apr. 17, 1989, now abandoned, which is itself a continuation-in-part of Ser. No. 222,016, filed Jul. 21, 1988, now U.S. Pat. No. 4,921,710, issued May 1, 1990.

BACKGROUND OF THE INVENTION

It is generally recognized that high blood cholesterol concentrations provide a significant risk factor in heart disease. It is also generally recognized that eating foods high in saturated fats, like many red meats, may contribute significantly to increased blood cholesterol concentrations in humans. Correspondingly, the increased blood cholesterol concentration in humans seems to have a direct positive correlation with coronary heart disease. Accordingly, there is a continuing and real interest in decreasing the intake of food substances that have high cholesterol content. Thus, there has been in the past years a significant health trend away from red meat, milk products, and eggs. Accordingly, there is a continuing and real need to develop techniques for decreasing cholesterol concentrations in these foods.

Cholesterol reductase is a known enzyme that catalyzes the chemical reduction of cholesterol to coprostanol. However, heretofore, it has been believed and found that cholesterol reductase is present only in certain bacteria. In my earlier filed application, it was reported that it had been discovered that cholesterol reductase is present in certain green plant parts, particularly the leaves of green leafy plants, such as soybeans, corn, and cucumbers. It is believed that in my earlier application we were the first ever to discover and take advantage of the existence of cholesterol reductase in green plant parts.

In my earlier application, the invention was premised upon a method of decreasing cholesterol concentration in meat by administering to meat animals just prior to slaughter a substantial dose of cholesterol reductase. This can be thought of as an "indirect" means of treating cholesterol concentration in humans. The present application is premised upon a more direct route that involves oral capsule administration of cholesterol reductase to humans.

It is a primary objective of the present invention to provide an oral method of administration of cholesterol reductase to humans such that the delivery system bypasses the stomach and releases cholesterol reductase in the small intestine to convert cholesterol in the lumen of the small intestine to coprostanol, which is poorly absorbed.

Another objective of the present invention is to administer to humans via the proximal small intestine, cholesterol reductase to convert cholesterol to coprostanol.

Another objective of the present invention is to provide a delivery system for cholesterol reductase that is resistant to degradation by the acid and the proteolytic enzymes of the stomach such that it does not release the within-contained cholesterol reductase until the capsules, pills, or the like have passed from the stomach into the small intestine.

A further objective is to use a substance to protect the cholesterol reductase from the proteolytic activity in the small intestine.

An even further objective of the present invention is to decrease the health risk of people that use meats and other animal products used as food, such as swine, poultry, fish, eggs, and milk products, by decreasing the cholesterol concentration within the body of the food product consumer.

The method and means of accomplishing each of the above objectives as well as others will become apparent from the detailed description of the invention that follows hereinafter.

SUMMARY OF THE INVENTION

Figure 1:
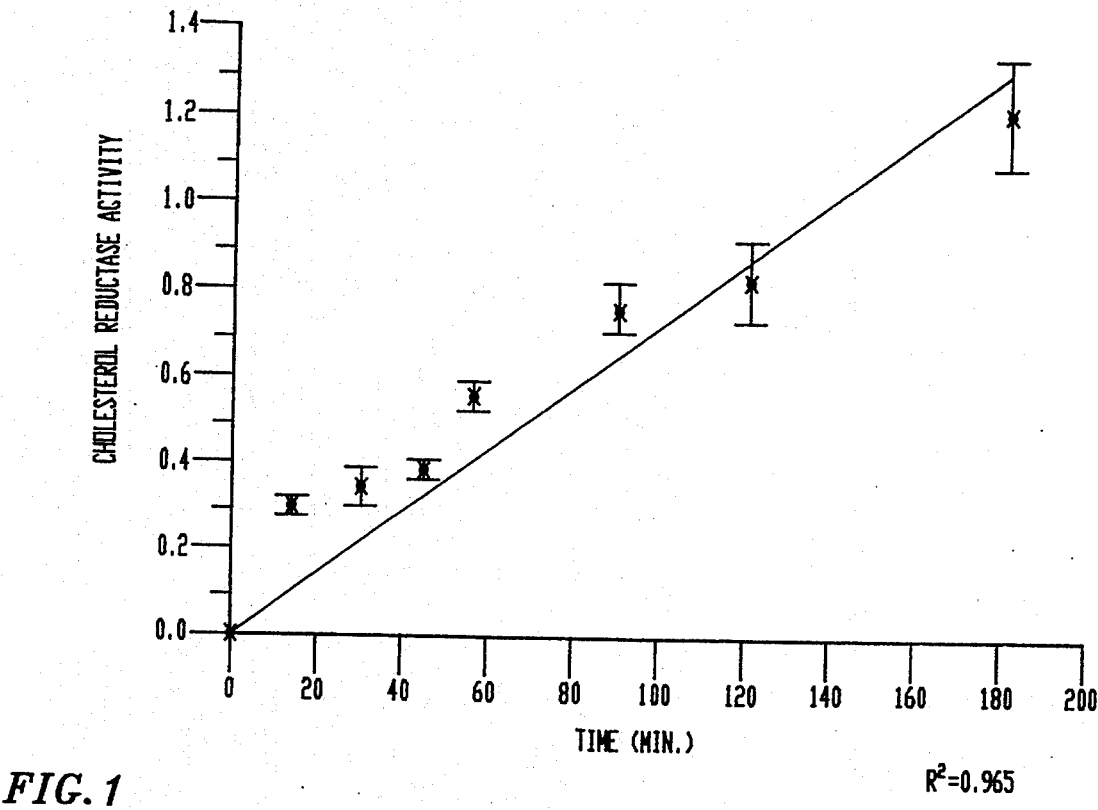
FIG. 1 is a graph showing cholesterol conversion to coprostanol in cream over a designated time period.

Preferrably pure preparations of cholesterol reductase are encapsulated in a dose delivery system that markedly decreases the probability of release of cholesterol reductase in the human stomach, but increases the probability of release of cholesterol reductase into the proximal small intestine to convert cholesterol in the lumen of the small intestine to coprostanol, which is poorly absorbed. Alternatively, the delivery system can use a molecular-sieve like material which allows the cholesterol present in the small intestine to diffuse into the molecular sieve matrix, thus allowing the enzyme to convert it to coprostanol which is poorly absorbed.

DETAILED DESCRIPTION OF THE INVENTION

In accordance with the process of my earlier invention, cholesterol reductase was extracted from green plant parts by homogenizing the green plant parts in an isotonic aqueous-based buffered salt solution that generally has a pH in the range from about 6.0 to about 7.5. For details of that extraction and homogenization process, see the disclosure of my related application Ser. No. 222,016 (now U.S. Pat. No. 4,921,710), which is incorporated herein by reference. Alternatively, the cholesterol reductase may be prepared from a naturally occurring bacteria such as Eubacteria species.

As explained in my earlier application, for commercial production of cholesterol reductase the gene or genes for cholesterol reductase in plants or bacteria may be transferred into another easy-to-grow bacterial species such as E. coli. The process would be similar to that now in use for making human insulin, bovine growth hormone, and porcine growth hormone.

The concentrate can be further treated to obtain substantially 100% pure cholesterol reductase by using conventional separation and concentration techniques. Substantial purity is preferred because the delivery system involves oral dosing of humans.

Coprostanol is normally produced in the intestine of animals. It represents cholesterol that has been hydrogenated. Coprostanol is poorly absorbed by humans, and the reduction of cholesterol to coprostanol is enhanced by the enzymatic activity of cholesterol reductase.

Cholestyramine and colestipol are effective hypocholesterolemic agents because they increase the excretion of sterols, especially bile acids. Average humans consume about 700 mg of cholesterol, secrete about 1,000 mg of cholesterol into the small intestine by way of bile, and "slough" about 400 mg of cholesterol into the intestinal lumen by way of sloughed intestinal epithelial cells. Therefore, endogenous cholesterol contributes significantly to the pool of cholesterol in the small intestine that is available for absorption.

Introduction of cholesterol reductase into the proximal small intestine will convert cholesterol in the lumen of the small intestine to coprostanol, which is poorly absorbed.

In one embodiment of the invention, purified cholesterol reductase is encapsulated in a specific polymeric material to form a delivery pill or capsule that is resistant to degradation by the gastric acidity and pepsin but is degraded with concommitant release of cholesterol reductase by higher pH and bile acids in the contents of the proximal small intestine. Cholesterol reductase then catalyzes conversion of cholesterol present in the small intestine to coprostanol. The cholesterol reductase could be protected from proteolytic activity in the small intestine by protease inhibitors added to the delivery dose. Alternatively, the cholesterol reductase could be encapsulated in a molecular sieve-like material by which cholesterol transverses the sieve material to become acted upon by cholesterol reductase. The proteolytic enzymes in the lumen are unable to transverse the sieve, and thus the cholesterol reductase is protected from proteolytic degradation. Because coprostanol is poorly absorbed, the cholesterol homeostasis of the human or other animal is stressed to the point of high probability for a hypocholesterolemic response.

The amount of active cholesterol reductase preparation in the delivery dose should vary depending upon body weight. It should be an amount sufficient to effectively reduce cholesterol to coprostanol. However, generally speaking, the amount will vary from about 0.001 mg/kg of body weight to about 10.0 mg/kg of body weight, preferably from 0.01 mg/kg of body weight to about 1 mg/kg of body weight, and most preferrably from about 0.05 mg/kg of body weight to about 0.5 mg per/kg of body weight.

Pharmaceutical carriers that are acid resistant to the acid pH of the stomach, which normally is about 2, may be used. They also should be nondigestible to the enzyme pepsin, which is present in the stomach. There are commercially available solid pharmaceutical carriers that are resistant to stomach degradation and will pass through to the small intestine where the bile in the intestine, which is more lipophilic, will dissolve them. See for example Viokase and Entozyme that are marketed by A. H. Robins Company of Richmond, Va. These compounds are examples of carriers that dissolve in the small intestine but not in the stomach. Another potential coating is marketed by Lactaid, Inc. of Pleasantville, N.J. The preferred carriers are solid carrier materials, and flavor materials may be added to those.

Solid pharmaceutical carriers such as starch, sugar, talc, mannitol and the like may be used to form powders. Mannitol is the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of the active enzyme and may be administered one or more at a time at regular intervals. Such unit dosage forms, however, should generally contain a concentration of 0.1% to 10% by weight of one or more of the active cholesterol reductase enzyme.

A typical tablet may have the composition:

|   | Mg. |
| --- | --- |
| 1. Cholesterol reductase | 12.5 |
| 2. Mannitol | 100 |
| 3. Stearic acid | 3 |

A granulation is made from the mannitol. The other ingredients are added to the dry granulation and then the tablets are punched.

Another tablet may have the composition:

|   | Mg. |
| --- | --- |
| 1. Cholesterol reductase | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   | Mg. |
| --- | --- |
| 1. Cholesterol reductase | 5 |
| 2. Lactose U.S.P. | 200 |
| 3. Starch U.S.P. | 16 |
| 4. Talc U.S.P. | 8 |

In another alternative and equally preferred embodiment, a substantially inert molecular sieve material is utilized. The matrix of the molecular sieve is such that the cholesterol reductase stays within the molecular sieve and cholesterol present in the small intestine diffuses into the sieve because it is of smaller molecules. Once inside of the sieve, the cholesterol reductase acts upon the cholesterol to convert it to coprostanol, which is not absorbed in the small intestine but passes through. Preferred molecular sieve materials are Sephadex or Sephadex that has been made more hydrophilic through derivatization. (Pharmacia Inc. currently markets such products.)

The following examples are offered to illustrate but not limit the process of the invention.

EXAMPLES

Figure 2:
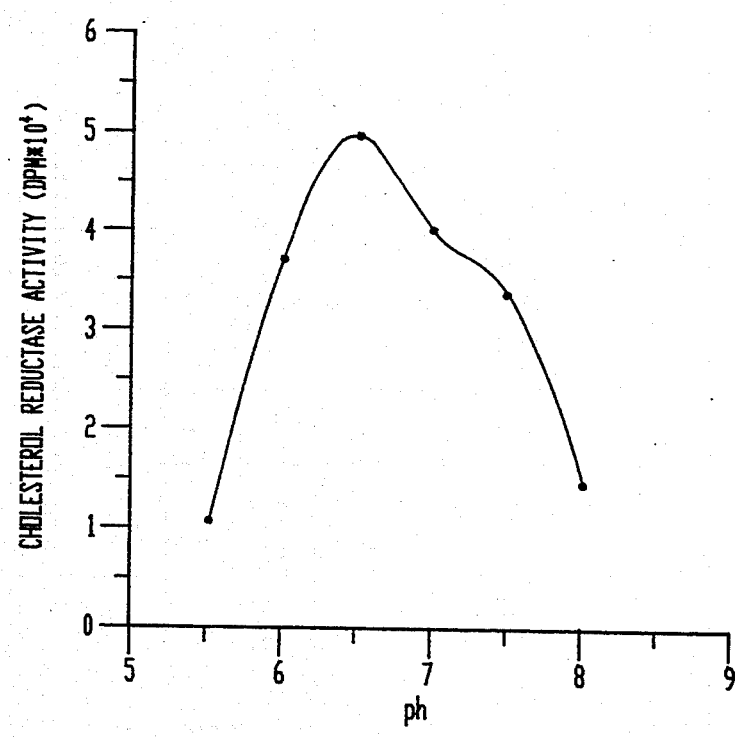
FIG. 2 is a graph showing cholesterol reductase activity as a function of pH.

This example shows that cholesterol reductase will reduce cholesterol in food to coprostanol. Cholesterol reductase activity was tested for its maximal activity at various pH values. The activity was measured by quantifying the amount of radioactive cholesterol that is converted to radioactive coprostanol. The amount of coprostanol synthesized is expressed as $DPM \times 10^4$ which is a measure of radioactivity, and is shown in FIG. 2. There, it can be seen that the maximal activity is at a pH of 6.5. This is also the normal pH of the intestinal contents located a few inches from the site where the acidic contents of the stomach flow into the "opening" of the small intestine.

In addition to testing activity of cholesterol reductase at various pHs, cholesterol reductase was added to known high cholesterol foods in small amounts such as cream, ground meats, egg yolk and milk, and thereafter on a time basis synthesis of coprostanol was monitored. FIG. 1 shows synthesis of coprostanol in cream over time by addition of cholesterol reductase and thereafter measuring the nmoles of coprostanol present in the incubation mixture. There, it can be seen that cholesterol in cream was converted to coprostanol and that the amount of coprostanol conversion increased linearly and significantly over time. Other data from another experiment that shows coprostanol synthesis from cholesterol in cream are shown in Table I below.

TABLE I

Conversion of Cholesterol in Cream to Coprostanol

| | Synthesis of coprostanol nmoles/hr | Cholesterol converted to coprostanol (%) |
|---|---|---|
| Cream + C.R.[a] | 0.085 ± 0.0096 | 0.01 ± 0.0017 |
| Cream + C.R. + NADH[b] | 1.09 ± 0.125 | 0.2 ± 0.02 |

[a] Added 45 nmoles/hr. of cholesterol reductase (C.R.) activity.
[b] Increased NADH concentration by 1 mM.

This second experiment again demonstrated coprostanol synthesis in a dairy food and stimulation of that synthesis by NADH, a naturally occurring reducing agent. Similarly, other foods were treated with cholesterol reductase in a 1-hour incubation at 37° C., and the coprostanol synthesis was measured in DPM/hr. As before, DPM is a measure of synthesis of radioactive coprostanol from radioactive cholesterol. These results are shown in Table II below.

TABLE II

Treatment of Foods with "Cholesterol Reductase"

| Source of cholesterol reductase/Food | Coprostanol Synthesized* dpm/hr |
|---|---|
| Human Fecal Culture: | |
| Milk | 410 |
| Ground Beef | 226 |
| Horse Fecal Culture: | |
| Milk | 970 |
| Alfalfa Leaves: | |
| Milk | 927 |
| Ground Beef | 168 |
| Cucumber Leaves: | |
| Milk | 564 |
| Ground Beef | 2,320 |
| Egg Yolk | 1,757 |

This experiment indicates that cholesterol reductase from several biological sources can be used to convert cholesterol in foods to coprostanol.

Because the pH and the ionic strength of intestinal contents and incubation mixtures in these studies were similar to those of the environment of the intestine, this work strongly indicates that cholesterol reductase in the intestinal contents of a human will convert dietary as well as endogenous cholesterol to coprostanol. Moreover, the coprostanol, once synthesized, by the cholesterol reductase conversion, will not be absorbed in the intestine, see Bhattacharyya, A. K., "Difference in Uptake and Esterification of Saturated Analogues of Cholesterol By Rat Small Intestine", Am. J. Physiol. 251:G495-G500 (1986).

In addition, it is highly unlikely that the bile acids would serve as a substrate for cholesterol reductase. This is true because bile acids are not a substrate for cholesterol oxidase, which is used in standard assays for concentration of cholesterol in blood, which also contains bile acids. Bile acids are highly water soluble compounds, whereas cholesterol is water insoluble. This physical difference alone will give rise to substrate specificity differences. Furthermore, bile acids do not contain the double bond as in cholesterol for reduction by the cholesterol reductase. (See standard biochemistry texts for chemical structures of bile acids.)

The purified cholesterol reductase will have been encapsulated with the molecular sieve-like material. The "capsule" remains intact during transfer from the mouth to the person's intestinal lumen. The "encapsulated" cholesterol reductase thus becomes located in the small intestine where the dietary and endogenous cholesterol are presented for absorption by the small intestinal mucosa. This cholesterol along with reducing agents, such as nicotinamide adenine dinucleotide, nicotinamide adenine dinucleotide phosphate, or ascorbic acid, diffuse through the material and coprostanol production results. Alternatively, the reducing agents may be incorporated within the capsule with the enzyme. Coprostanol will tend to diffuse out of the capsule so that during the time the capsule resides in the intestinal lumen much of the cholesterol will be converted to coprostanol for excretion in the feces.

What is claimed is:

1. A unit dosage pharmaceutical composition comprising a pharmaceutical carrier that is encapsulated in a solid carrier and is resistant to degradation in the environment of the stomach but capable of degradation in the environment in the small intestine, and from about 0.001 mg to 10.0 mg of purified cholesterol reductase per kilogram of body weight.

2. The unit dosage pharmaceutical composition of claim 1 wherein the unit dose also contains an effective amount of a protease inhibitor in order to increase the lifetime of the cholesterol reductase in the intestine.

3. The unit dosage pharmaceutical composition of claim 1 wherein said pharmaceutical carrier is a molecular sieve material so that the cholesterol can diffuse to the site of cholesterol reductase.

4. The pharmaceutical composition of claim 1 wherein said solid pharmaceutical carrier is selected from the group consisting of lactose, starch, sugar, talc, and mannitol.

5. A method of controlling human blood cholesterol levels, said method comprising;
   (a) orally administering a cholesterol reducing effective amount of purified cholesterol reductase to human patients;
   (b) said cholesterol reductase being encapsulated in a pharmaceutically acceptable carrier material that is resistant to degradation in the stomach but is capable of release of cholesterol reductase for interaction with cholesterol in the proximal region of the small intestine to convert cholesterol to insoluble coprostanol.

6. The method of claim 5 wherein the amount of cholesterol reductase is from 0.001 mg to 10.0 mg/kg of body weight.

* * * * *